United States Patent [19]
Varma et al.

[11] 3,994,935
[45] Nov. 30, 1976

[54] STEROIDAL 16β-ALKYL[16α,17-b]NAPHTHALENES

[75] Inventors: Ravi K. Varma, Belle Mead; Christopher M. Cimarusti, Hamilton, both of N.J.

[73] Assignee: E. R. Squibb & Sons, Inc., Princeton, N.J.

[22] Filed: Nov. 24, 1975

[21] Appl. No.: 634,684

[52] U.S. Cl.............................. 260/397.3; 260/397.45
[51] Int. Cl.² ........................................... C07J 1/00
[58] Field of Search................... 260/397.3, 397.45

[56] References Cited
UNITED STATES PATENTS
3,944,584   3/1976   Chao et al. ................... 260/397.3

*Primary Examiner*—Elbert L. Roberts
*Attorney, Agent, or Firm*—Lawrence S. Levinson; Merle J. Smith; Donald J. Barrack

[57] ABSTRACT

Novel steroids having the structure

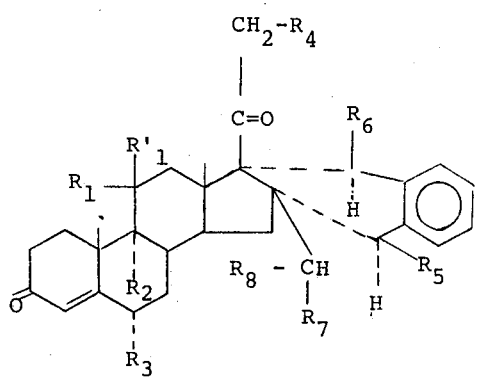

and the 1,2-dehydro derivatives thereof, wherein $R_1$ is chlorine, fluorine, or hydroxy and $R'_1$ is hydrogen or $R_1$ and $R'_1$ together are =O; $R_2$ is hydrogen or halogen; $R_3$ is hydrogen, methyl, or fluorine; $R_4$ is hydrogen, hydroxy,

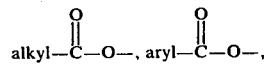

or halogen; $R_5$ and $R_6$ are the same or different and are hydrogen, alkyl, alkoxy, carboalkoxy, formyl,

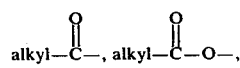

hydroxy, halogen, phenyl or cyano, with the proviso that when $R_5$ and $R_6$ are different, one of $R_5$ and $R_6$ is hydrogen; and $R_7$ and $R_8$ are the same or different and are hydrogen or alkyl.

8 Claims, No Drawings

STEROIDAL 16β-ALKYL[16α,17-B]NAPHTHALENES

BRIEF DESCRIPTION OF THE INVENTION

Steroidal 16β-alkyl[16α,17-b]naphthalenes having the structure I

I

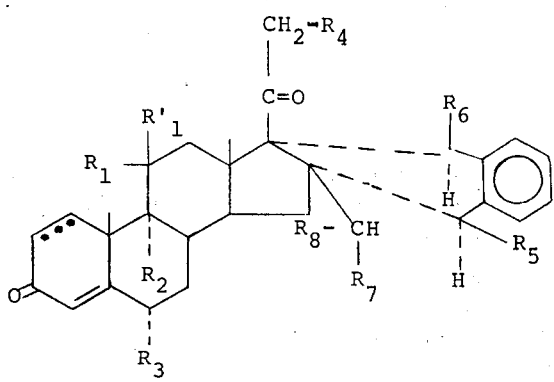

are useful topical and systemic anti-inflammatory agents. In formula I, and throughout the specification, the symbols are as defined below:

$R_1$ is chlorine, fluorine or hydroxy and $R'_1$ is hydrogen or $R_1$ and $R'_1$ together are =O;

$R_2$ is hydrogen or halogen;

$R_3$ is hydrogen, methyl or fluorine;

$R_4$ is hydrogen, hydroxy,

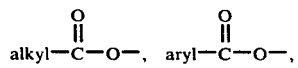

or halogen;

$R_5$ and $R_6$ are the same or different and are hydrogen, alkyl, alkoxy, carboalkoxy, formyl,

hydroxy, halogen, phenyl or cyano, with the proviso that when $R_5$ and $R_6$ are different, one of $R_5$ and $R_6$ is hydrogen; and $R_7$ and $R_8$ are the same or different and are hydrogen or alkyl.

The dotted line in the 1,2-position of the steroid of formula I represents the optional presence of ethylenic unsaturation.

The term "alkyl," as used throughout the specification, refers to straight or branched chain hydrocarbon groups having 1 to 6 carbon atoms.

The term "alkoxy," as used throughout the specification, refers to groups having the formula Y-O— wherein Y is alkyl as defined above.

The term "aryl," as used throughout the specification, refers to phenyl or phenyl substituted with alkyl, alkoxy, or halogen; phenyl is preferred.

The term "halogen," as used throughout the specification, refers to fluorine, chlorine, bromine, and iodine; fluorine, chlorine, and bromine are preferred.

DETAILED DESCRIPTION OF THE INVENTION

The steroids of formula I are physiologically active substances which possess glucocorticoid and anti-inflammatory activity and hence can be used in lieu of known glucocorticoids in the treatment of rheumatoid arthritis, for which purpose they can be administered in the same manner as hydrocortisone, for example, the dosage being adjusted for the relative potency of the particular steroid. In addition, the steroids of this invention can be used topically in lieu of known glucocorticoids in the treatment of skin conditions such as dermatitis, psoriasis, sunburn, neurodermatitis, eczema, and anogenital pruritus.

When given orally, the compounds of this invention may be used in a dosage range of 0.1 to 200 milligrams, preferably 0.3 to 100 milligrams. If administered topically, the compounds of this invention may be used in the range of 0.01 to 5.0% by weight, preferably 0.05 to 2.0% by weight, in a conventional cream or lotion.

The steroids of formula I (and the 1,2-dehydro derivatives thereof) wherein $R_4$ is other than hydroxy can be prepared by reacting a benzocyclobutene having the structure

II

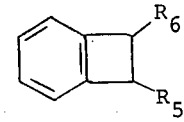

with a steroid having the structure

III

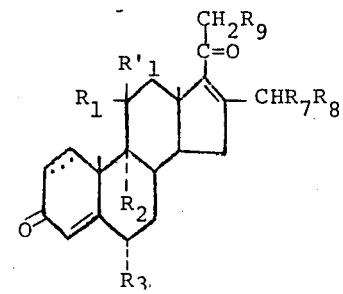

to yield a steroid having the structure

IV

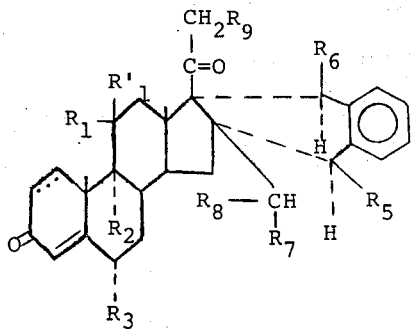

In formulas III and IV, and throughout the specification, $R_9$ can be hydrogen,

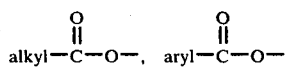

or halogen. The above reaction can be run with or without an inert solvent. Preferably, the reaction will be run neat, in an inert atmosphere, at temperatures up to the boiling point of the solution.

Those steroids of formula I wherein $R_4$ is hydroxy or halogen can be prepared from the corresponding 21-acyloxy steroid of formula IV. Hydrolysis of the 21-acyloxy steroid yields the corresponding 21-hydroxy steroid which can in turn be converted to a 21-halo steroid using procedures well known in the art.

Alternatively, the compounds of formula I (and the 1,2-dehydro derivatives thereof) can be prepared from benzocyclobutenes of formula II and steroids having the structure

V

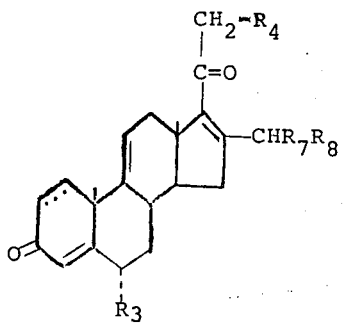

Reaction of a benzocyclobutene of formula II and a steroid of formula V yields a novel steroidal intermediate having the structure VI

VI

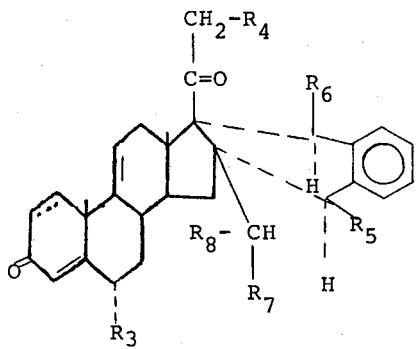

A steroid of formula VI can be converted to the corresponding 9,11β-dihalo steroid or 9-halo-11β-hydroxy steroid using procedures well known in the art. The 21-acyloxy steroids can be readily converted to the corresponding 21-hydroxy and 21-halo steroids.

The steroids of formulas III and V can be prepared from a corresponding steroid starting material having the structure

VII

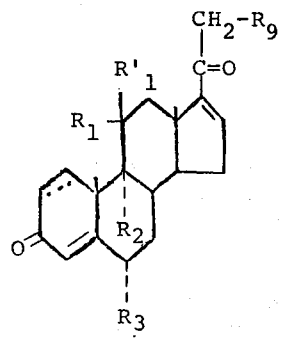

or

VIII

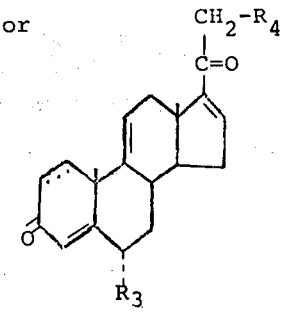

Reaction of a steroid of formula VII (or an 11β-acyloxy derivative thereof) or formula VIII with a diazoalkane having the formula

$N_2\text{-CHR}_7R_8$      IX yields a pyrazoline steroid having the structure

X

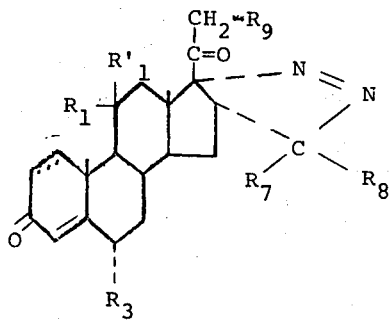

or

XI

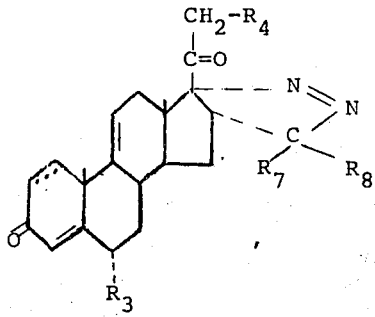

which can be heated to yield a 16β-alkylpregnene of formula III or V.

Many variations of the above-described procedures for preparing the steroids of this invention will be apparent to a person of ordinary skill in the steroid art.

The following examples are specific embodiments of this invention.

EXAMPLE 1

9-Fluoro-1',2',3',4'-tetrahydro-11β,21-dihydroxy-16β-methyl-pregna-1,4-dieno[16α,17-b]naphthalene-3,20-dione

A.

11β,21-bis(Acetyloxy)-9-fluoro-4',5'-dihydropregna-1,4-dieno-[17,16α-c][3H]pyrazole-3,20-dione A solution of 250 ml of ethereal diazomethane [from 25 g of N-methyl-N-nitroso-N'-nitroguanidine] is diluted with 550 ml of dichloromethane and 7.0 g of 11β,21-bis(acetyloxy)-9-fluoropregna-1,4,16-triene-3,20-dione is added. The solution is stirred at room temperature for 1 hour. Acetic acid is added until the yellow color of the solution disappears. The solvent is removed in vacuo and the residue redissolved in dichloromethane. The dichloromethane solution is washed with a saturated sodium bicarbonate solution, dried over anhydrous sodium sulfate and evaporated in vacuo to give 8.0 g of the title compound.

B.

11β,21-bis(Acetyloxy)-9-fluoro-16-methylpregna-1,4,16-triene-3,20-dione

11β,21-bis(Acetyloxy)-9-fluoro-4',5'-dihydropregna-1,4-dieno-[17,16α-c][3H]pyrazole (7.5 g) is stirred at 175° C (oil bath temperature) for 3 hours in 100 ml of ethylene glycol. The solution is cooled and diluted with 100 ml of chloroform and water. The chloroform layer is separated and the aqueous layer is washed with chloroform. The chloroform solutions are combined, washed with water, dried over anhydrous sodium sulfate and evaporated in vacuo to give 7.2 g of a foam which is dissolved in 9:1 chloroform-hexane and chromatographed on a 110 g-silica gel column. Elution with 1:1 chloroform-hexane and 3:2 chloroform-hexane gives 4.3 g of the title compound, melting point 240°–241° C.

C.

9-Fluoro-1',2',3',4'-tetrahydro-11β,21-dihydroxy-16β-methylpregna-1,4-dieno[16α,17-b]naphthalene-3,20-dione A mixture of 1 g of 11β,21-bis(acetyloxy)-9-fluoro-16-methylpregna-1,4,16-triene-3,20-dione and 6.5 ml of benzocyclobutene is stirred at 185° C (oil bath temperature) under nitrogen for 7 days. The solution is cooled, diluted with 3:1 chloroform-hexane and chromatographed on an 80 g silica gel column. Elution with 1:1 chloroform-hexane gives 640 mg of material as a foam. This is dissolved in a mixture of methanol (20 ml) and tetrahydrofuran (20 ml), a 10% potassium carbonate solution (0.6 ml) is added and the mixture is stirred at room temperature under nitrogen for 6 hours. The resulting solution is neutralized with 3% acetic acid. The solvent is partially removed in vacuo to give 490 mg of the title compound. Crystallization from chloroform-methanol gives the analytical sample of the title compound, melting point 306°–307° C.

EXAMPLE 2

21-(Acetyloxy)-9-fluoro-1',2',3',4'-tetrahydro-11β-hydroxy-16β-methylpregna-1,4-dieno[16α,17-b]naphthalene-3,20-dione A solution of 280 mg of 9-fluoro-1,',2',3',4'-tetrahydro-11β,21-dihydroxy-16β-methylpregna-1,4-dieno[1-6α,17-b]naphthalene-3,20-dione and 0.3 ml of acetic anhydride in 25 ml of pyridine is stirred at room temperature under nitrogen for three hours. The resulting solution is poured into cold 5% hydrochloric acid and extracted with chloroform. The chloroform solution is washed with water, dried over anhydrous sodium sulfate and evaporated in vacuo to give a foam. This is dissolved in 1:3 hexane-chloroform and chromatographed on a 40 g silica gel column. Elution with hexane-chloroform (1:3 to 1:4) gives 243 mg of material. Crystallization from ethyl acetate-hexane gives 212 mg of the title compound, melting point 169°–178° C.

EXAMPLE 3

4',21-bis-(Acetyloxy)-6α-fluoro-11β-hydroxy-16β-propyl-1',2',3',4'-tetrahydropregna-1,4-dieno[16α,17-b]naphthalene-3,20-dione

A.

21-(Acetyloxy)-3'-ethyl-6α-fluoro-4',5'-dihydro-11β-hydroxypregna-1,4-dieno[17,16α-c][3H]pyrazole-3,20-dione A solution of 21-(acetyloxy)-6α-fluoro-11β-hydroxypregna-1,4,16-triene-3,20-dione (748 mg, 2.0 mmol) in dichloromethane is stirred at room temperature and a solution of 1-diazopropane (6 mmol) in ether is added. Stirring is continued for about 3 hours, and excess diazopropane is then decomposed by the addition of the requisite amount of acetic acid. The solvent is evaporated yielding the title compound.

B.

21-(Acetyloxy)-6α-fluoro-11β-hydroxy-16-propyl-pregna-1,4,16-triene-3,20-dione 21-(Acetyloxy)-3'-ethyl-6α-fluoro-4',5'-dihydro-11β-hydroxypregna-1,4-dieno[17,16α-c][3H]pyrazole-3,20-dione (850 mg) is suspended in ethylene glycol (20 ml) and stirred in a bath at 175° C for 3 hours. The resulting solution is cooled, diluted with water, and extracted with chloroform. The chloroform extract is absorbed on a column of silica gel (30 g) and the column is eluted successively with chloroform-hexane and chloroform to yield the title compound.

C.

4',21-bis-(Acetyloxy)-6α-fluoro-11β-hydroxy-16β-propyl-1',2',3',4'-tetrahydropregna-1,4-dieno[16α,17-b]naphthalene-3,20-dione A solution of 21-(acetyloxy)-6α-fluoro-11β-hydroxy-16-propylpregna-1,4,16-triene-3,20-dione (2.0 mmol) in o-dichlorobenzene (30 ml) is heated with 1-acetyloxybenzocyclobutene (6.0 mmol) in a bath at 170° C for 3 days. The resulting solution is cooled, diluted with chloroform-hexane and absorbed on a column of silica gel (50 g). The column is eluted successively with chloroform-hexane, chloroform, and chloroform-ethyl acetate to yield the title compound.

EXAMPLE 4

21-(Acetyloxy)-11β-chloro-9-fluoro-16β-isopropyl-1',2',3',4'-tetrahydropregna-1,4-dieno[16α,17-b]naphthalene-3,20-dione

A.

21-(Acetyloxy)-4',5'-dihydro-3',3'-dimethylpregna-1,4,9-(11)-trieno[17,16α-c][3H]pyrazole-3,20-dione A solution of 21-(acetyloxy)pregna-1,4,9(11),16-tetraene-3,20-dione (2.0 mmol) in dichloromethane is stirred at room temperature and a solution of 2-diazopropane (6 mmol) in ether is added. Stirring is continued for about 3 hours, and excess diazopropane is then decomposed by the addition of the requisite amount of acetic acid. The solvent is evaporated yielding the title compound.

B.

21-(Acetyloxy)-16-isopropylpregna-1,4,9(11),16-tetraene-3,20-dione 21-(Acetyloxy)-4',5'-dihydro-3',3'-dimethylpregna-1,4,9(11)-trieno[17,16α-c][3H]pyrazole-3,20-dione (2.0 mmol) is suspended in ethylene glycol (25 ml) and stirred in a bath at 175° C for about 3 hours. The resulting solution is cooled, diluted with water, and extracted with chloroform. The chloroform extract is absorbed on a column of silica gel (30 g) and the column is eluted successively with chloroform-hexane and chloroform to yield the title compound.

C.

21-(Acetyloxy)-16β-isopropyl-1',2',3',4'-tetrahydropregna-1,4,9(11)-trieno[16α,17-b]naphthalene-3,20-dione A solution of 21-(acetyloxy)-16-isopropylpregna-1,4,9(11),16-tetraene-3,20-dione (1.0 mmol) in benzocyclobutene (15 ml) is refluxed under a nitrogen atmosphere for 6 days. After cooling, the mixture is subjected to column chromatography on silica gel to isolate the title compound.

D.

21-(Acetyloxy)-11β-chloro-9-fluoro-16β-isopropyl-1',2',3',4'-tetrahydropregna-1,4-dieno[16α,17-b]naphthalene-3,20 -dione A suspension of 21-(acetyloxy)-16β-isopropyl-1',2',3',4'-tetrahydropregna-1,4,9(11)-trieno[16α,17-b]naphthalene-3,20-dione (2.0 mmol) and N-chloroacetamide (2.2 mmol) in dry dichloromethane (30 ml) is added over a 2–3 minute period with stirring to a mixture of anhydrous hydrogen fluoride (12 g) in dry tetrahydrofuran (20 ml) in a polyethylene bottle at −78° C. After 1.0 hour of stirring, the mixture is maintained at 0° C for 1.0 hour and poured into an ice cold sodium bicarbonate solution. Extraction with dichloromethane followed by column chromatography on silica gel yields the title compound.

EXAMPLES 5–16

Following the procedure of Example 3, but substituting the steroid listed in column I for 21-(acetyloxy)-6α-fluoro-11β-hydroxypregna-1,4,16-triene-3,20-dione, the compound listed in column II for 1-diazopropane, and the compound listed in column III for 1-acetyloxybenzocyclobutane, yields the steroid listed in column IV.

| Example | Column I | Column II | Column III | Column IV |
| --- | --- | --- | --- | --- |
| 5 | 21-(acetyloxy)-6α,9-difluoro-11β-hydroxypregna-1,4,16-triene-3,20-dione | diazomethane | 1-cyanobenzocyclobutene | 21-(acetyloxy)-6α,9-difluoro-11β-hydroxy-16β-methyl-3,20-dioxo-1',2',3',4'-tetrahydropregna-1,4-dieno[16α,17-b]-naphthalene-4'β-carbonitrile |
| 6 | 9-fluoro-11β-hydroxy-6α-methylpregna-1,4,16-triene-3,20-dione | diazomethane | 1-carbomethoxybenzocyclobutene | 9-fluoro-1',2',3',4'-tetrahydro-11β-hydroxy-6α,16β-dimethyl-3,20-dioxopregna-1,4-dieno[16α,17-b]naphthalen-4'β-oic acid, methyl ester |
| 7 | 21-(acetyloxy)-9-fluoro-11β-hydroxypregna-1,4,16-triene-3,20-dione | diazomethane | trans-1,2-diethoxybenzocyclobutene | 21-(acetyloxy)-1'β,4'β-diethoxy-9-fluoro-1',2',3',4'-tetrahydro-11β-hydroxy-16β-methylpregna-1,4-dieno[16α,-17-b]naphthalene-3,20-dione |
| 8 | 21-(acetyloxy)-9-fluoro-11β-hydroxypregna-1,4,16-triene-3,20-dione | 1-diazobutane | 1-carbomethoxybenzocyclobutene | 21-(acetyloxy)-16β-butyl-9-fluoro-1',2',3',4'-tetrahydro-11β-hydroxy-3,20-dioxopregna-1,4-dieno[16α,17-b]naphthalene-4'β-oic acid, methyl ester |
| 9 | 21-(acetyloxy)-9-fluoro-11β-hydroxypregna-1,4,16-triene-3,20-dione | 1-diazohexane | trans-1,2-dicarbomethoxybenzocyclobutene | 21-(acetyloxy)-9-fluoro-16β-hexyl-1',2',3',4'-tetrahydro-11β-hydroxy-3,20-dioxopregna-1,4-dieno[16α,17-b]naphthalene-1'β,4'β-dioic acid, dimethyl ester |
| 10 | 21-(acetyloxy)-9-fluoro-11β-hydroxypregna-1,4,16-triene-3,20-dione | diazomethane | trans-1,2-dibromobenzocyclobutene | 21-(acetyloxy)-1'β,4'β-dibromo-9-fluoro-1',2',3',4'-tetrahydro-11β-hydroxy-16β-methylpregna-1,4-dieno[16α,17-b]naphthalene-3,20-dione |
| 11 | 21-(acetyloxy)-9-fluoro-11β-hydroxypregna-1,4,16-triene-3,20-dione | diazomethane | 1-acetylbenzocyclobutene | 21-(acetyloxy)-4'-acetyl-16β-ethyl-9-fluoro-1',2',-3',4'-tetrahydro-11β-hydroxypregna-1,4-dieno[16α,17-b]-naphthalene-3,20-dione |
| 12 | 21-(acetyloxy)-9-fluoro-11β-hydroxypregna-1,4,16-triene-3,20-dione | diazomethane | 1-bromobenzocyclobutene | 21-(acetyloxy)-4'β-bromo-9-fluoro-1',2',3',4'-tetrahydro-11β-hydroxy-16β-methyl- |

-continued

| Example | Column I | Column II | Column III | Column IV |
|---|---|---|---|---|
| 13 | 21-(acetyloxy)-6α-methylpregna-1,4,16-triene-3,11,20-trione | diazomethane | 1-formylbenzocyclobutene | pregna-1,4-dieno[16α,17-b]-naphthalene-3,20-dione 21-(acetyloxy)-4′β-formyl-1′,2′,3′,4′-tetrahydro-6α,-16β-dimethylpregna-1,4-dieno[16α,17-b]naphthalene-3,11,20-trione |
| 14 | 21-chloro-11β-hydroxypregna-4,16-diene-3,20-dione | diazomethane | 1-phenylbenzocyclobutene | 21-chloro-1′,2′,3′,4′-tetrahydro-11β-hydroxy-16β-methyl-4′β-phenylpregn-4-eno[16α,17-b]-naphthalene-3,20-dione |
| 15 | 21-(benzoyloxy)-11β-hydroxypregna-1,4,16-triene-3,20-dione | diazomethane | 1-ethylbenzocyclobutene | 21-(benzoyloxy)-4′β-ethyl-1′,2′,3′,4′-tetrahydro-11β-hydroxy-16β-methylpregna-1,4-dieno[16α,17-b]naphthalene-3,20-dione |
| 16 | 21-chloro-11β-hydroxypregna-4,16-diene-3,20-dione | diazomethane | 1-benzocyclobutenol | 21-chloro-1′,2′,3′,4′-tetrahydro-4′β,11β-dihydroxy-16β-methylpregn-4-eno[16α,17-b]-naphthalene-3,20-dione |

What is claimed is:

1. A steroid having the formula

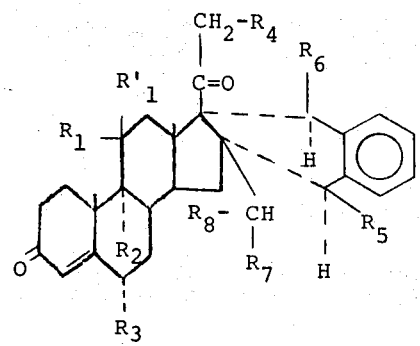

or the 1,2-dehydro derivatives thereof, wherein $R_1$ is chlorine, fluorine or hydroxy and $R'_1$ is hydrogen, or $R_1$ and $R'_1$ together are =O; $R_2$ is hydrogen or halogen; $R_3$ is hydrogen, methyl or fluorine; $R_4$ is hydrogen, hydroxy,

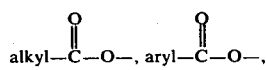

or halogen; $R_5$ and $R_6$ are the same or different and are hydrogen, alkyl, alkoxy, carboalkoxy, formyl,

hydroxy, halogen, phenyl or cyano, with the proviso that when $R_5$ and $R_6$ are different, one of $R_5$ and $R_6$ is hydrogen; and $R_7$ and $R_8$ are the same or different and are hydrogen or alkyl.

2. A steroid in accordance with claim 1 wherein $R_7$ and $R_8$ are hydrogen.

3. A steroid in accordance with claim 1 wherein $R_1$ is hydroxy and $R'_1$ is hydrogen.

4. A steroid in accordance with claim 1 wherein $R_3$ is hydrogen.

5. A steroid in accordance with claim 1 wherein $R_2$ is fluorine.

6. The steroid in accordance with claim 1 having the name 9-fluoro-1′,2′,3′,4′-tetrahydro-11β, 21-dihydroxy-16β-methylpregna-1,4-dieno[16α, 17-b]naphthalene-3,20-Dione.

7. The steroid in accordance with claim 1 having the name 21-(acetyloxy)-9-fluoro-1′,2′,3′,4′-tetrahydro-11β-hydroxy16β-methylpregna-1,4-dieno[16α,17-b]naphthalene-3,20-dione.

8. A steroid having the formula

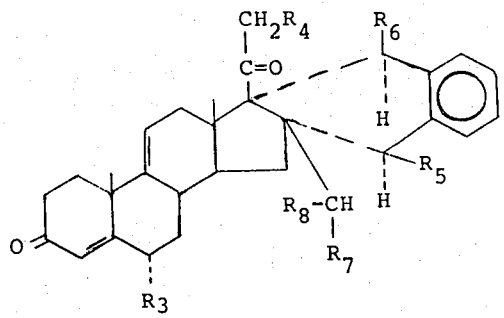

or the 1,2-dehydro derivative thereof, wherein $R_3$ is hydrogen, methyl, or fluorine; $R_4$ is hydrogen, hydroxy,

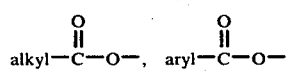

or halogen; $R_5$ and $R_6$ are the same or different and are hydrogen, alkyl, alkoxy, carboalkoxy, formyl,

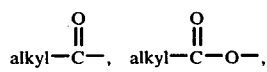

hydroxy, halogen, phenyl, or cyano, with the proviso that when $R_5$ and $R_6$ are different, one of $R_5$ and $R_6$ is hydrogen; and $R_7$ and $R_8$ are the same or different and are hydrogen or alkyl.

* * * * *